United States Patent [19]
Boldt

[11] Patent Number: 5,282,460
[45] Date of Patent: Feb. 1, 1994

[54] THREE AXIS MECHANICAL JOINT FOR A POWER ASSIST DEVICE

[75] Inventor: Kenneth Boldt, Allentown, Pa.

[73] Assignee: Joyce Ann Boldt, Allentown, Pa.

[21] Appl. No.: 818,646

[22] Filed: Jan. 6, 1992

[51] Int. Cl.⁵ .......................... A61H 1/00; A61F 2/74
[52] U.S. Cl. ..................................... 128/25 R; 623/26;
623/66; 403/52; 403/122; 403/119
[58] Field of Search ................. 128/782, 25 R, 25 B,
128/44, 53, 56, 67; 482/51, 66; 602/2, 20, 23,
32; 623/24–26, 18–19, 66; 901/1, 28–29;
73/379; 403/52, 112, 114, 119, 122, 164–165,
75, 58, 77, 124–126

[56] References Cited

U.S. PATENT DOCUMENTS

| | | |
|---|---|---|
| 1,880,138 | 9/1932 | Hubl . |
| 2,879,995 | 3/1959 | Harrison, III ........................ 403/119 |
| 3,358,678 | 12/1967 | Kultsar . |
| 3,449,769 | 6/1969 | Mizen . |
| 3,477,171 | 11/1969 | Bonanno ............................. 403/112 |
| 4,180,870 | 1/1980 | Radulovic . |
| 4,557,257 | 12/1985 | Fernandez . |
| 4,676,798 | 6/1987 | Noiles ............................. 623/19 X |

Primary Examiner—Richard J. Apley
Assistant Examiner—John P. Leubecker
Attorney, Agent, or Firm—Eckert Seamans Cherin & Mellott

[57] ABSTRACT

An exoskeletal robotic device supplements relative movement between biological skeletal members coupled at a biological joint of a wearer, and preferably forms complete sections of a skeleton to be worn by a human. First and second frame members for mechanical joints are attachable to the wearer adjacent the biological joint. The mechanical joints define a center of relative rotation of the frame members about at least two, and preferably three mutually perpendicular axes, the center of relative rotation of the frame members being displaced from the outer surfaces of the skeletal members to correspond in position with the center of the biological joint. Actuation devices in the form of hydraulic cylinders are coupled between the first and second frame members for rotating the frame members under power under control of a microprocessor which can execute stored sequences or apply power in the same direction as exerted by the wearer against pressure sensors coupled to the microprocessor. The mechanical joint includes spherical guide surfaces defining a slidable connection of the frame members, and having a radius intersecting the center of the biological joint.

24 Claims, 9 Drawing Sheets

THREE AXIS MECHANICAL JOINT FOR A POWER ASSIST DEVICE

BACKGROUND OF THE INVENTION

1. Field of the Invention

This invention relates to the field of power assist apparatus to be attached to human beings and the like, for assisting the application of muscle power to move skeletal joints. In particular the invention provides power assist apparatus that is mechanically coupled to the wearer in a manner that aligns the application of force by the apparatus to the rotational axes of the wearer's joints.

2. Prior Art

Exoskeletal power assist devices are known, for example, from U.S. Pat. No. 1,880,138 Hübl; U.S. Pat. No. 3,358,678 Kultsar; U.S. Pat. No. 3,449,769—Mizen; U.S. Pat. No. 4,180,870—Radulović; and U.S. Pat. No. 4,557,257—Fernandez et al. These disclosures range from Hübl, wherein the device is much larger than the operator or "wearer", to Kultsar, wherein the device is embodied as a form-fitting suit including power applying apparatus. The general object may be to sense the application of force from the wearer's muscle power, and to operate a power assist mechanism that applies force in the same direction, i.e., to multiply the force applied by the wearer. Alternatively, the device may provide controlled joint displacement for a wearer whose muscles or nerves are inoperative for applying force in a desired direction.

Power assist devices of this kind may rely on the wearer's skeletal joints for constraining movement of the skeletal members at a joint, namely with power assisting actuators being fixed relative to the wearer's skeletal members The opposite ends of an extendible/retractable actuator are attached respectively to the wearer on opposite sides of the joint. The means to which the ends of the actuator are attached may define at least a partial rigid supplemental skeletal member which is attached along the user's limbs or the like on opposite sides of one or more joints. An actuator coupled to a controller applies power to the supplemental skeletal member(s) to cause relative rotation of the wearer's skeletal members about the joint. For a more heavy duty application, the device may have a more complete version of the skeletal members, in the form of rigid structures which are placed alongside the user's skeletal members and are attached to one another at joints which supplement the wearer's joints. For a knee supplement, for example, a first rigid member is attached along the femur and a second rigid member is attached along the tibia and fibula, the two rigid members being affixed to one another via a hinging joint. Similarly, and elbow supplement would have an external humerus attachment hinged to a radius/ulna attachment. Whereas the rigid members are themselves jointed, the supplement does not rely on the wearer's joints for sole support.

Devices of this type can be used by persons with weakened muscles or those with nervous system problems which limit the extent to which the person can apply muscular force. Paraplegics, persons having a portion of a limb amputated, aged persons, convalescents and the like can all benefit from power assist devices. In addition, healthy persons can use devices of this type in order to increase their muscle power as needed to perform functions requiring more than normal muscle power or stamina. For example, workmen with power assist devices can lift and carry greater loads, soldiers can carry extra ammunition or body armor, and so forth. These capabilities are achieved without the user operating a separate piece of equipment for lifting, carrying, etc. The wearer's action is intended to be similar to natural muscular and skeletal action, but at greater power.

Where a power assist orthosis is coupled directly to a wearer, the application of force must be limited by the degrees of freedom of the wearer's joints. Prior art attempts to provide power assist devices have been characterized by mechanisms which define idealized and limited rotation axes. The natural degrees of freedom of human joints are not reflected in the joints of the external skeletal members. In Kultsar, for example, the mechanisms associated with the hip joints, knees, elbows, etc. each have only one respective degree of freedom. The mechanism for the hips, for example, defines on each opposite side of the body a rotation axis parallel to the ground surface and passing laterally along the line of the wearer's hip joints. The power applied by the device is thus limited to causing the femur to swing forward or backward parallel to a vertical plane including the hip joint of the apparatus.

However, the hip joint has additional degrees of freedom, as do other joints of the body. The proximal or hip end of the femur defines a laterally inward bend terminating in a ball which engages the pelvic bone in a ball and socket joint. The hip joint is thus a universal joint capable of positioning the femur at any angle relative to the pelvis and also can rotate the femur relative to its longitudinal axis, subject to maximum limits of angular displacement defined by the ball and socket structures of the joint.

The respective degrees of freedom of a joint can be described with reference to the mutually perpendicular axes of a cartesian coordinate system. A joint such as the hip, shoulder or wrist permits: lateral/medial displacement (for example in the hip joint of a standing person, the rotation of the femur about a substantially vertical axis); flexion/extension (swinging of the leg from front to back about a horizontal axis aligned transversely of the person); and, abduction/adduction (swinging of the leg outwardly and inwardly about a horizontal axis extending forward and rearward). Natural movements such as walking typically include components in each of these degrees of freedom.

If a supplemental joint is modeled to accommodate only certain of the degrees of freedom, it is not possible for the wearer to move naturally. In Kultsar, wherein a hip joint permits only flexion/extension, it is difficult or impossible for the wearer to balance or to move normally using the device. Therefore, even though supplemental power assists in forward/rearward swinging of the leg, the apparatus cannot be used effectively to assist a person in walking or otherwise carrying on normal activities with power assist.

The respective joints vary in their natural limits of displacement as well as in their levels of freedom around the respective axes mentioned. Whereas the hip and shoulder are substantially universal joints, the elbow for example is limited in freedom of abduction/adduction, free in flexion/extension above the aligned position of the forearm and upper arm. Due to the arrangement of the radius and ulna, the forearm between the wrist and elbow is quite free in lateral/medial displacement, allowing rotation of the wrist.

Although it is possible to couple force exerting actuators directly to the user's limbs as described, it is not advantageous in a power assist device to couple to a human joint an external jointed fixture which has the same degrees of freedom as the joint. Whereas the external joint would define degrees of freedom which are centered on the external joint rather than on the biological joint, power applied to the external skeletal members by such a device seeks to move the skeletal members about axes intersecting at the universal joint of the external skeleton rather than axes intersecting at the biological joint. The external device exerts unnatural and potentially injurious force on the bones at the joint because the force is not aligned to axes of freedom of the actual joint between the wearer's skeletal members. An external universal joint of mechanical skeletal members placed alongside the hip joint, for example, defines a center which is displaced laterally from the center of the biological hip joint. As a result, any from the center of the biological hip joint. As a result, any force applied to the external universal joint applies tensile or compressive forces between the two bones of the biological joint. Similar results accrue in other joints. A flexion/extension joint for an elbow, for example, can be placed laterally alongside the elbow, but placing it over or under the elbow applies compression or tension between the bones at the elbow joint, and so forth. In short, it is difficult to accurately reflect the degrees of freedom of a biological joint in an exoskeletal joint, primarily due to the inherent necessity that the exoskeletal joint, which is external to the wearer, be displaced from the biological joint. The problem is acute where a joint has two or more degrees of freedom.

SUMMARY OF THE INVENTION

It is an object of the present invention to provide a mechanical joint which is displaced from a biological joint, in particular because the mechanical joint is external to the wearer, wherein the mechanical joint accurately reflects the degrees of freedom of the biological joint.

It is also an object of the invention to provide an external mechanical joint which defines at least two mutually perpendicular axes of rotation, using structures located outside of the biological joint, wherein the axes intersect the center of the biological joint.

It is another object of the invention to provide a universal joint with a displaced center of rotation about three mutually perpendicular axes.

It is yet another object of the invention to provide a displaced-center joint mechanism, including means for applying force thereto, which is generally applicable to the joints of humans and animals.

It is a further object of the invention to provide a substantially complete power-assist exoskeleton apparatus which enables a user to perform most of the activities of a biological muscular and skeletal arrangement, at increased power.

It is still a further object of the invention to provide a displaced center exoskeletal joint having arcuate sliding surfaces defining a universal joint motion about a center axis displaced from the joint, the arcuate sliding surfaces having a radius about the center axis dimensioned such that the joint can supplement a biological joint.

These and other objects are provided by an exoskeletal robotic device that supplements relative movement between biological skeletal members coupled at a biological joint of a wearer, and preferably forms complete sections of a skeleton to be worn externally by a human. First and second frame members for a mechanical joint are attachable to the wearer's limb or the like adjacent to the biological joint. The mechanical joints define centers of relative rotation of the frame members about at least two, and preferably three mutually perpendicular axes, the respective center of relative rotation of the frame members at a joint being displaced from the outer surfaces of the skeletal members to correspond in position with the center of rotation of the biological joint. Actuation devices in the form of hydraulic cylinders are coupled between the first and second frame members for rotating the frame members under power. Preferably the actuation members are compact rack and pinion drive mechanisms having paired opposed cylinders on the frame members for driving rotation over a predetermined range. The actuation devices can be controlled at least partly by a microprocessor which can execute stored sequences. Alternatively or in addition, the actuation devices can apply power in the same direction as exerted by the wearer against pressure sensors coupled to control valves which may also be operable via the microprocessor. The microprocessor enables modification of user-controlled motions so as to simulate gravity effects. The mechanical joint preferably includes spherical guide surfaces defining a slidable connection of the frame members, the guide surfaces having a radius intersecting the center of the biological joint. Flexion can be driven by rotating a joint housing about a flexion axis defined by one of two frame members at a joint, while medial displacement and adduction are driven by rotating the opposed frame member relative to the joint housing using the guide surfaces. In a preferred embodiment medial displacement is driven by an eccentric engaging a slide slot while adduction is driven by a length-adjustable connection between the opposed frame member and the joint housing, spaced from the guide surfaces.

BRIEF DESCRIPTION OF THE DRAWINGS

There are shown in the drawings the embodiments of the invention as presently preferred. It should be understood that the preferred embodiments are exemplary and not limiting. Reference should be made to the appended claims in order to assess the scope of the invention and its reasonable equivalents. In the drawings.

DETAILED DESCRIPTION OF THE PREFERRED EMBODIMENTS

Figure 1:
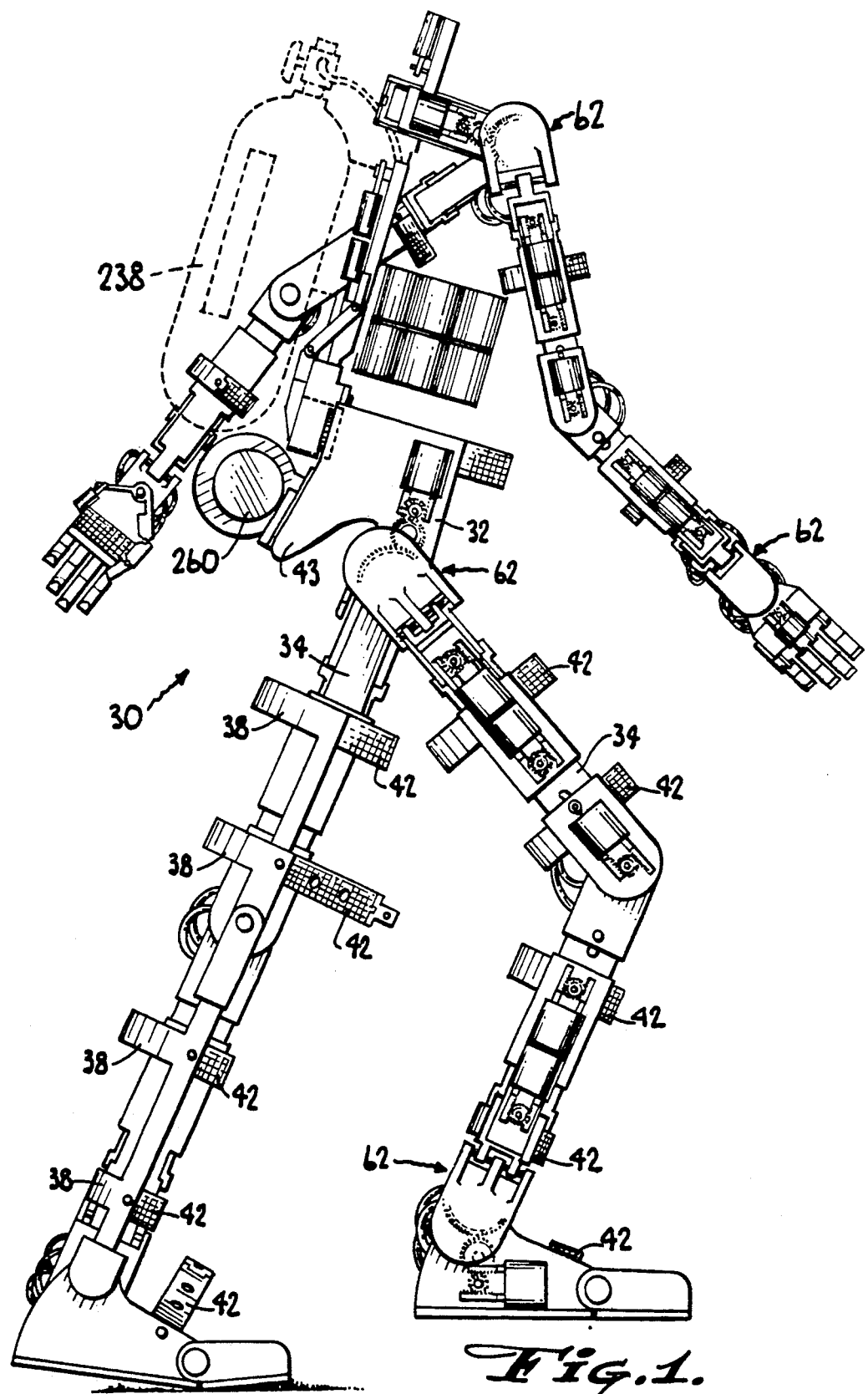
FIG. 1 is a side elevation schematic view illustrating a substantially complete exoskeleton robotic device according to the invention.
Figure 12:
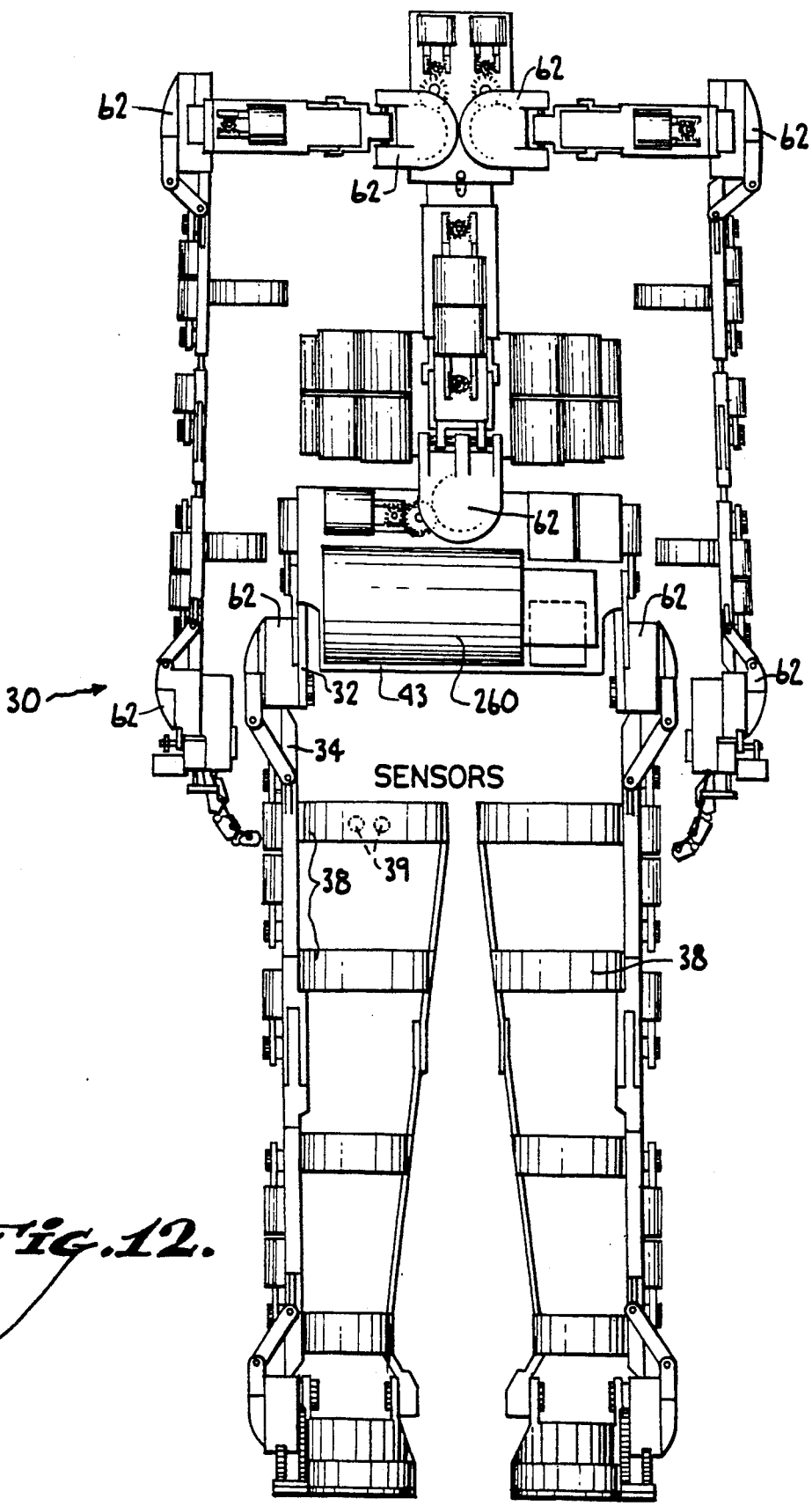
FIG. 12 is a rear elevation view of the complete exoskeleton of FIG. 1, shown upright.

FIGS. 1 and 12 illustrate a complete exoskeleton robotic device 30 according to the invention, and in particular shows the points at which powered mechanical joints placed externally to the wearer's biological joints can provide support and assistance to the wearer in a manner aligned to the centers of rotation of the wearer's joints. Not all of the wearer's joints need be powered, and not all require a full three degrees of freedom. According to the preferred embodiment, three degrees of freedom and powered actuators can be provided for the outer ankle, hip, lumbar spine, shoulder and wrist. Bilateral three degree joints are also provided for a connection between the shoulders and the cervical spine, similar to a clavicle or shoulderblade arrangement at the rear. The knee and elbow have a single degree of freedom, i.e., flexion and extension. An inner ankle slip joint is provided simply for support in lieu of a powered joint. The sole can include a freely pivoting toe panel.

The joint of the invention can be applied to a single joint and is discussed herein with primary reference to particular exemplary joints. For example the hip joint is used as the primary example of a three degree joint. The same mechanical joint structure can be applied to the other three degree joints. Each biological joint involves two rigid biological skeletal members which are attached to form a joint wherein the biological skeletal members are relatively rotatable about one or more rotation axes. The exoskeleton of the invention provides two rigid mechanical members, attached to form first and second couplings, and means for attaching them rigidly to the wearer's skeletal members. The mechanical members are coupled at a mechanical joint which defines arcuate sliding surfaces centered on the biological joint. Although the center of the biological joint (which of course is internal) is spaced from the structures which attach the two mechanical members, the mechanical joint models the biological one.

The apparatus of the invention can be applied to a single joint or a bilateral pair of joints but preferably is applied to a plurality of joints which together enable at least a subset of the full range of normal human activities, for example at least walking or lifting. Assuming that the apparatus includes mechanical frame members which extend between two joints or from a joint to the distal end of a limb, and preferably between the various joints and limbs associated with ambulation and like, the mechanical frame members 32, 34 correspond to the wearer's bones. The frame members 32, 34 are substantially rigid lengths of metal or hard plastic, of sufficient strength and durability to withstand the expected load. It is possible to mount additional structures to the frame members, which may or may not have biological analogues. Body armor, receptacles for articles such as ammunition, grasping apparatus, etc. can be added in view of the capability for ambulation provided by the invention notwithstanding the increased weight.

According to the embodiment of FIGS. 1 and 12, the entire skeleton is worn by the user, being placed over and around the user from the rear. The frame members can have limb support cradles 38 which curve partway around the user's limbs, each being attached to the corresponding limb by a belt or strap 42 which wraps around the opposite side of the limb.

Figure 2:
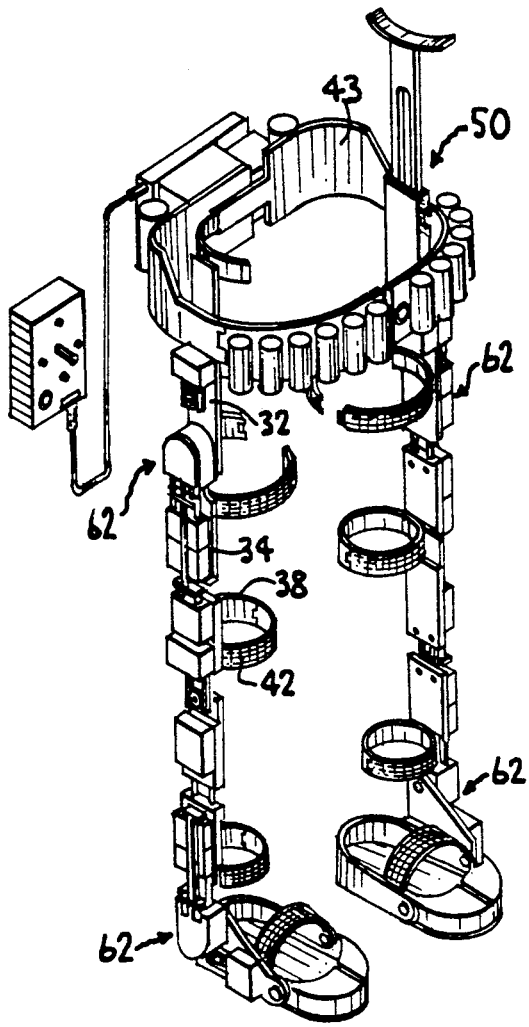
FIG. 2 is a perspective view of a pelvic and leg embodiment of the powered exoskeleton.

A partial exoskeleton arrangement 50 can be provided as shown in FIG. 2, in this case the exoskeleton being arranged only for engaging the pelvis, legs and feet as needed for walking or running. The respective frame members attach to the pelvis, at two spaced points along the femur and the tibia/fibula, as well as at the arch of the foot. The upper attachment device on the femur can encircle the thigh partially. The frame members otherwise define cradles 38 on one side, opposed by belts or straps 42 on the opposite side, for rigidly attaching to the wearer. The frame member 43 affixed to the pelvis includes means mounted on a front encircling strap for mounting batteries, and a miniature power source and controller for applying power to the actuators, mounted on the rear or pelvis cradle. The hip joints and the outer ankle joints define three degrees of freedom, and the knee joint operates only in flexion/extension. The knee joint includes mechanical stops for limiting the forward rotation of the tibia/fibula to a position substantially collinear with the femur, as in a natural knee joint. Whereas the knee requires only a hinging motion, the exoskeletal knee joint provides merely a pivoting motion and is mounted laterally adjacent the knee to define a rotation axis extending horizontally through the center of rotation of the biological knee joint. The physical engagement of the pelvis portion 43 of the exoskeleton 50 to the wearer can be further stabilized by extensible supports which protrude upwardly to reside against the wearers upper torso or at an armpit, as suggested in FIG. 2.

Preferably the exoskeleton 30 or 50 assists in such activities as walking, rising from or lowering oneself into a chair, traversing stairs, etc. For this purpose the exoskeleton can include sensors responsive to differential pressure of the wearer's limbs, the sensors being coupled to proportional valves disposed between the power source and the actuators for applying mechanical power to rotate the respective limbs around the joints in the same direction as the wearer urges his or her limbs. Alternatively or in addition, the controller can be arranged to read out preprogrammed sequences for effecting common sequences of motions. This latter alternative allows the exoskeleton to be operated by a person wholly lacking in motor or nerve function as to the respective limbs. Control of the actuators is discussed hereinafter, following a discussion of the mechanical operation of the joint.

Figure 4:
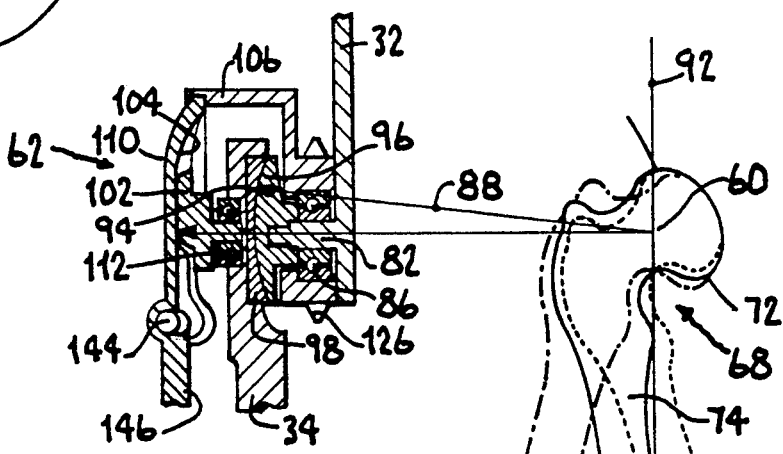
FIG. 4 is a partial longitudinal section view through a joint mechanism according to the invention, illustrated in connection with the ball and socket joint of a human hip.

According to the invention three degree of freedom mechanical joints are provided for those biological joints characterized by three degrees of freedom. Each three-degree mechanical joint 62 defines a center which corresponds to the center 60 of the biological joint with which the mechanical joint 62 is associated, as shown in FIG. 4 with reference to a hip joint 68. Although the exoskeleton provides support even when not powered, the joints preferably are provided with actuation mechanisms 66 that force angular displacement of the frame members 32, 34 associated with the joint. The actuation devices 66 can be length extendible and retractable devices such as hydraulic or pneumatic cylinders, which are each attached at points off the respective axis of rotation and thus force the frame members to rotate relative to one another around the joint. It is also possible to power the joints via electric motors. Preferably the joints are powered using hydraulic actuators that are coupled to the power source via proportionally controlled valves.

Figure 3:
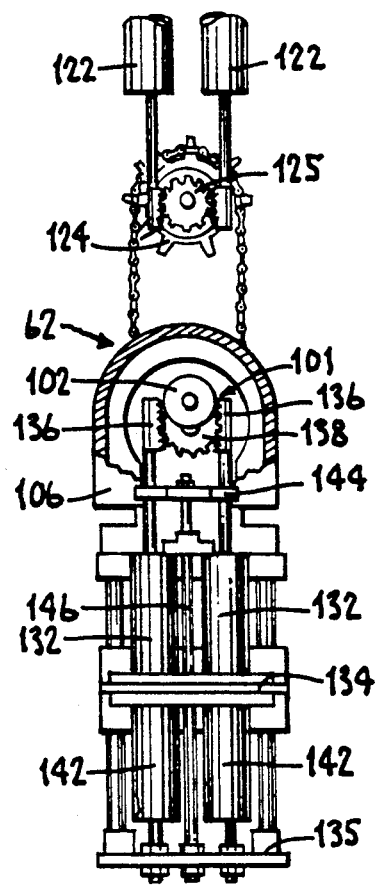
FIG. 3 is a partially cutaway schematic illustration of an actuation mechanism according to the invention for driving a joint in three degrees of freedom.

FIG. 3 is a partially cut away elevation view showing a preferred arrangement of actuation mechanisms for driving a joint in three degrees of freedom. Substantially the same joint structure is used for each of the three degree joints, and is discussed with reference to a hip joint 68 as an example. The biological hip joint is illustrated schematically in FIG. 4. The biological hip joint comprises a ball 72 at the end of the femur 74, which movably engages in a socket in the pelvis to provide a universal joint connection of the femur and the pelvis. Due to the muscle and tendon tissue (not shown) between the femur and the outer surface of the hip, and also due to the laterally inward angular crook 76 which occurs at the proximal end of the femur, the center of rotation of the ball and socket joint is displaced substantially from the area in which the mechanical joint 62 is located. The mechanical joint nevertheless is arranged such that the center of rotation of the mechanical joint corresponds with the center of rotation 60 of the biological joint.

In FIG. 4, the sectional view through the invention and through the hip joint 68 is along a vertical plane transverse to the wearer of the exoskeleton device. In order to permit flexion and extension, a horizontal shaft 82 and journal fitting including roller bearing 86 are arranged at the height of the center of the hip joint 68, defining a rotation axis that intersects the center 60 of the hip joint. The shaft 82 is coupled to one of the two frame members, i.e., frame member 32 which is fixed relative to the pelvis of the wearer by straps or belts. The other frame member 34 is fixed to the wearer on the opposite side of the joint. The bearing mechanism 86 is held in housing 106, which is attached to frame member 34. For example, frame member 32 is a rigid extension of the pelvis cradle 43 and frame member 34 is attached to the femur 74. The femur can swing forward and backward, with relative rotation of members 32, 34 at the rotation axis defined by shaft 82, intersecting the center of the ball and socket biological hip joint 68. This motion is displacement in flexion/extension of the joint.

For lateral/medial displacement or rotation of the leg about a vertical axis 92 through the center of the hip joint, and for adductor/abductor displacement, or rotation of the leg about a horizontal axis passing normally through the center of the hip joint, a concave socket 94 is provided on frame member 34, slidably engaged against a convex head member 96 disposed on the end of shaft 82. The concave/convex facing surfaces of socket 94 and head member 96 define a radius of curvature around the center 60 of the biological ball and socket joint. Slot 104 is provided in socket housing cap 110, slidably engaged against a convex shaped eccentric roller 102 rotatably attached to frame member 34. The concave/convex facing surfaces of slot 104 and eccentric roller 102 also defines a radius of curvature around center 60 of the biological ball and socket joint. These surfaces described may define sections of an inner sphere and outer sphere, respectively, with each having its center at the center of the biological joint. Effectively, the concave/convex surfaces define an outer ball and socket joint, but the operative guidance surfaces are spaced radially from the center of rotation of the biological joint. These surfaces allow the femur 74 to be rotated relative to the pelvis around a vertical axis 92 intersecting the center 60 of the joint, and around a horizontal axis passing normally through the center 60 of the joint. Preferably, a shock absorbing and/or wear resistant material 98 such as ultra high molecular weight polyethylene is employed for shock absorbing and wear resistant properties.

For guiding adduction and abduction of the femur, i.e., for swinging the femur laterally outwardly or inwardly, the vertical arcuate channel formed by the concave surface of slot 104 and the convex surface of head member 96 constrains frame member 34, via slidable engagement to the arcuate channel by the convex-surfaced eccentric roller 102 and by the concave-surfaced socket 94, to rotate upward or downward around a horizontal axis passing normally through the center 60 of the biological joint.

For guiding lateral/medial motion of the femur, i.e., for swinging the femur forward or backward, an eccentric roller assembly 101 having a cogwheel 138 as its base and an eccentric roller 102 is rotatably coupled to the lower frame member 34 by bearing 112 as shown in FIGS. 3 and 4. As the cogwheel 138 is rotated, the eccentric roller 102, being fixedly attached thereto, is caused to move concentrically about the rotational axis of cogwheel 138. Since the eccentric roller 102 is constrained within slot 104 from moving backward or forward, such rotation of cogwheel 138 causes the lower frame member 34, via slidable engagement of socket 94 with head member 96, to rotate forward or backward around a vertical axis 92 intersecting the center 60 of the biological joint.

The foregoing motions are simultaneously possible because the freedom of movement around each of the three mutually perpendicular axes is independent. Therefore, regardless of the angle of flexion around shaft 82, the lower frame 34 can be displaced outwardly or laterally/medially rotated, etc. Preferably, mechanical stops are defined by the mechanical joint are provided at slightly less than the maximum displacement of the biological joint for each respective axis, such that when powered the exoskeleton does not exert force against the wearer's bones once the natural limits of displacement are reached.

The operative connection of the driving actuators and the structures of the joint are illustrated in FIG. 3. The extension/flexion drive assembly comprises a pair of extensible cylinders 122 having one end coupled to the associated frame member and the opposite end coupled, for example via a rack and pinion arrangement, to a gear 125 fixed on a toothed sprocket 124. The sprocket 124 is coupled to the joint housing 106 by a chain loop which extends around the housing 106, engaging a corresponding toothed sprocket 126 attached to or formed on the outside of the joint housing 106, concentric with shaft 82. The extensible cylinders 122 are preferably hydraulic cylinders, operable in opposite directions, whereby the two are redundantly arranged. By operating the cylinders 122 in opposite directions, the sprocket 124, and therefore the sprocket 126 and the joint housing 106, are rotated relative to shaft 82 for causing flexion or extension. The flexion drive (like the adduction and medial drives) can also be locked at a given position by closing valves coupling the hydraulic fluid source to the cylinders such that the cylinders are held in fixed position.

Figure 5:
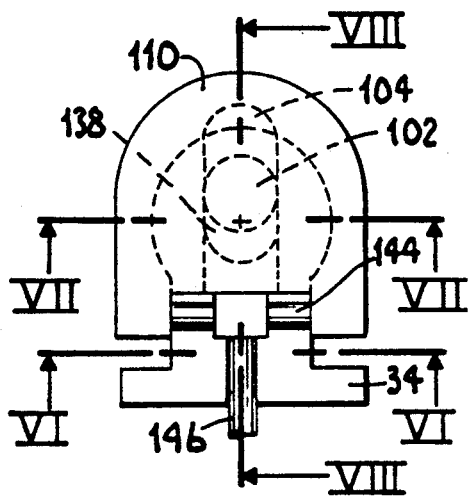
FIG. 5 is a partial elevation view of the joint mechanism as shown in FIG. 4.
Figure 6:
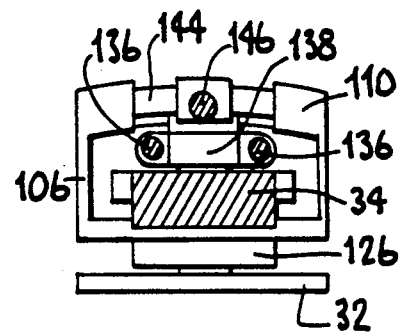
FIG. 6 is a partial section view along line VI—VI in FIG. 5, illustrating the medial drive section.
Figure 7:
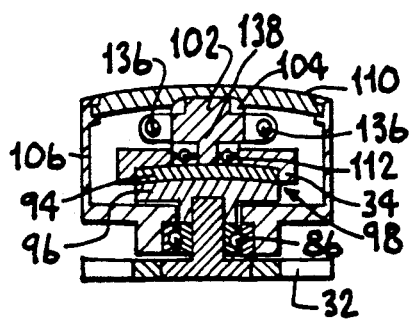
FIG. 7 is a partial section view along line VII—VII in FIG. 5.

As discussed above, the powered medial drive assembly is comprised of the eccentric roller assembly 101, which has a base 138 which is concentric with the rotation axis of the eccentric roller assembly, and an eccentric roller 102 which slides upwardly and downwardly in the slot 104 formed in the socket housing cap 110. The slot 104 is aligned longitudinally relative to frame member 34. Slot 104 is only larger than the eccentric roller 102 by a sufficient clearance to permit sliding. FIGS. 5-7 are helpful in envisioning the operation of the medial drive as well as the flexion and adduction drives. Slot 104 is shown in FIG. 4 but is part of the section of housing 106 which is cut away in FIG. 3. FIG. 5 shows the respective arrangement of the eccentric roller and slot, as well as the adduction drive shaft 146.

With powered rotation of base 138, the eccentric roller 102 (which is rigidly attached to base 138) is forced forward or rearward, driving lateral/medial displacement of frame member 34. In particular, the roller 102 forces frame member 34 to rotate relative to center 60 by sliding forward or rearward on the curving slide face defined between head member 96 and socket member 94.

The adduction drive bar 146 is attached relative to the lower frame member 34, while the joint housing 106 is attached relative to the upper frame member 32. To allow the two to move relative to one another during medial displacement, the adduction drive bar 146 can be attached to the joint housing 106 via arched adduction link pin 144, on which the end of drive bar 146 can be arranged to slide over a limited displacement. The opposite end of drive bar 146 can be attached to a sliding cross member 135 which moves longitudinally relative to frame member 34 with extension or retraction of adduction drive cylinders 142. The upper ends of drive cylinders 142 are fixed to cross member 134.

Medial drive cylinders 132 are coupled between the frame member 34 at cross member 134, which is rigidly mounted to the frame member 34, and opposite sides of the base portion 138 of eccentric roller 102. Preferably the base portion 138 of the eccentric roller assembly forms or is attached to a sprocket or cog wheel. The coupling of the cylinders to the base portion 138 is via a rack and gear arrangement, the ends of the cylinder shafts carrying toothed racks 136, which engage with gear teeth on the base 138 of the roller assembly. When medial cylinders 132 are operated in opposite directions the eccentric portion of roller 102 bears against the walls of the slot 104 in the socket housing cap, causing the joint to rotate about a vertical axis 92 intersecting the center 60 of the biological joint 68. The medial cylinders 132 are also preferably operable in opposite directions or can be locked, enabling medial/lateral displacement and also the locking of the joint in fixed medial position.

The adduction/abduction drive cylinders 142 are mounted between the frame 34 at cross member 134 and a link pin 144, via adduction drive bar 146. See FIGS. 4 and 5, and the alternative embodiment shown in FIG. 8. The adduction drive cylinders 142 operate in the same direction, i.e., either extending or retracting the distance between cross member 134 and link pin 144. Whereas link pin 144 defines an attachment point located at a space from the frame 34 (to the left in FIG. 4), extending or retracting the distance between the mounting of the adjuction drive cylinders 142 and the link pin 144 causes the joint to swing laterally inwardly and outwardly, respectively. This also causes roller 102 to move downward or upward in slot 104. The roller 102 can drive medial displacement from any position in slot 104. Similarly, the adduction and medial drives, which are substantially mounted on lower frame member 34, can operate at any position of flexion defined by the flexion drive, which is fixed relative to the upper member 32.

Frame member 32 is referenced generally herein as the "upper" frame member and frame member 34 as the "lower" frame member. It will be appreciated that the actual orientation of the joint and whether one of the frame members is above the other at any given time, is not pertinent to the invention, these terms being used for convenience in discussing the drawings.

A number of variations on the joint are possible and only a few will be mentioned for purposes of illustration. Whereas two cylinders are preferred, single acting cylinders can be provided rather than redundantly acting cylinders, e.g., one driving extension and the other driving retraction, and one being operated at a given time, while the other is released. It is also possible to vary the specific mechanical couplings to achieve the same action. For a more compact device, the sprocket and chain arrangement of the flexion drive assembly can be replaced with a rack and gear arrangement similar to that used for the illustrated medial drive assembly. The illustrated embodiment is preferred, however, as it allows room for mounting the cylinders and provides adequate power. Furthermore, as shown in FIGS. 1 and 12, it is possible to place the drive cylinders of a rack and pinion or chain and sprocket arrangement at a convenient point around the pinion or sprocket which is driven. For example, the flexion drive cylinders for the lumbar spine and cervical joints are placed at right angles relative to the medial and adduction drive cylinders in FIG. 12, and the shoulder and outer ankle joint flexion drive cylinders are similarly placed in FIG. 1. In these joints the respective frame members nominally define a right angle, whereas for the hip joint the pelvis and femur are nominally collinear. As shown generally in FIG. 12, one or more additional spur gears can be interposed between the gear 125 (see FIG. 3) driven by the flexion drive cylinders 122 and the sprocket or gear 126 formed on or attached to the joint housing 106, for appropriately setting the mechanical advantage between the drive cylinders 122 and the joint housing 106.

Figure 8:
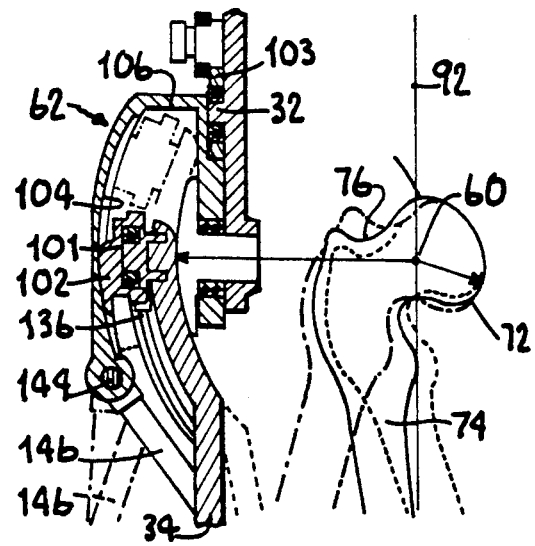
FIG. 8 is a partial section view of an alternative embodiment, corresponding to a view along line VIII—VIII in FIG. 5.

A first alternative embodiment for the three degree joint is shown in FIG. 8, with the same reference numbers used to identify corresponding structures as in FIGS. 3-7. According to this arrangement the lower frame member 34 defines a curve at the top. This embodiment requires the drive for medial displacement to operate laterally outwardly, above the plane of the lower part of frame member 34, so as to engage the gearwheel 138 at the base of the eccentric roller assembly 101. Additionally, a reduction gear 103 is interposed between the pinion gear of the flexion drive and the gear teeth on the outer wall of housing 106.

Figure 9:
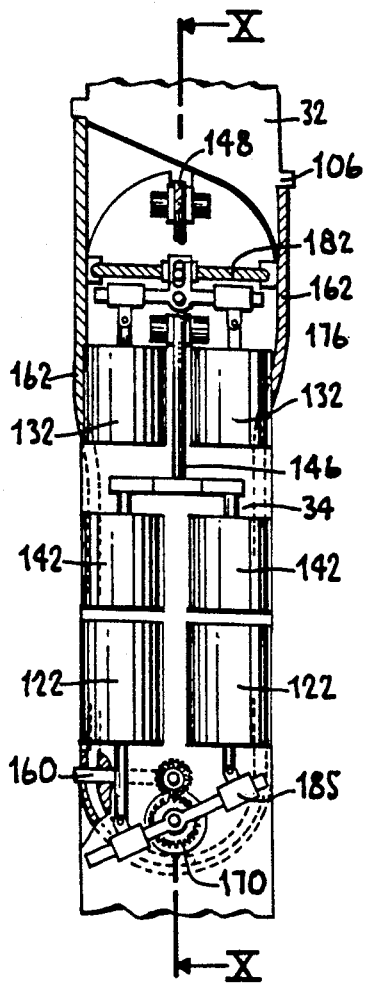
FIG. 9 is an elevation view showing an alternative embodiment of a joint mechanism according to the invention.
Figure 10:
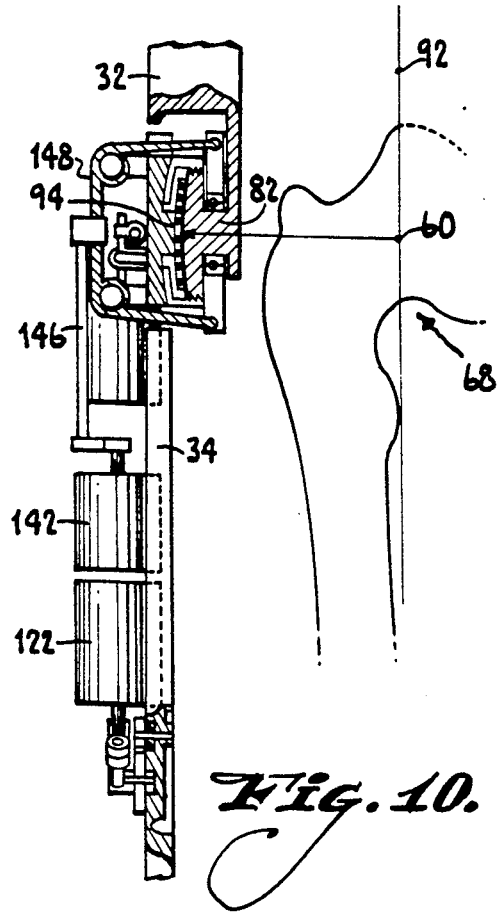
FIG. 10 is a section view along line X—X in FIG. 9.

Another alternative embodiment of the joint mechanism is shown in FIGS. 9 and 10. The same reference numbers again are used to identify elements corresponding to those of FIGS. 3-8; however the relative positions of the respective drive cylinders has been rearranged such that all are carried on the lower frame member 34. In the embodiment of FIGS. 9 and 10 the mechanical coupling of the actuator cylinders to the respective points on the joint is accomplished using cables. The cylinders are mounted to the frame members 32, 34 and the movable ends of the cylinders are coupled mechanically to the cables. An flexion/extension drive cable 162 is movable via connector 160 by extension drive cylinders 122. The arrangement includes a rocker assembly for guiding the connector 160 coupled to the cable 162. Movement of a rocker arm 185 is transferred through reduction gear assembly 170, for displacing the cable 162. The cable 162 is passed in a loop along a path which causes the cable to engage on the sides of joint housing 106, for pulling in either direction to cause rotation about the axis of the shaft 82.

For medial displacement a similar rocker and connector mechanism includes rocker 176 connected between the shaft ends of drive cylinders 132 and cable 182, and is operable to provide a force via cable 182 forcing the joint to rotate around the vertical axis 92 of the hip joint 68. The adduction drive cylinders 142 are coupled to cable 148 via drive bar 146.

Figure 11:
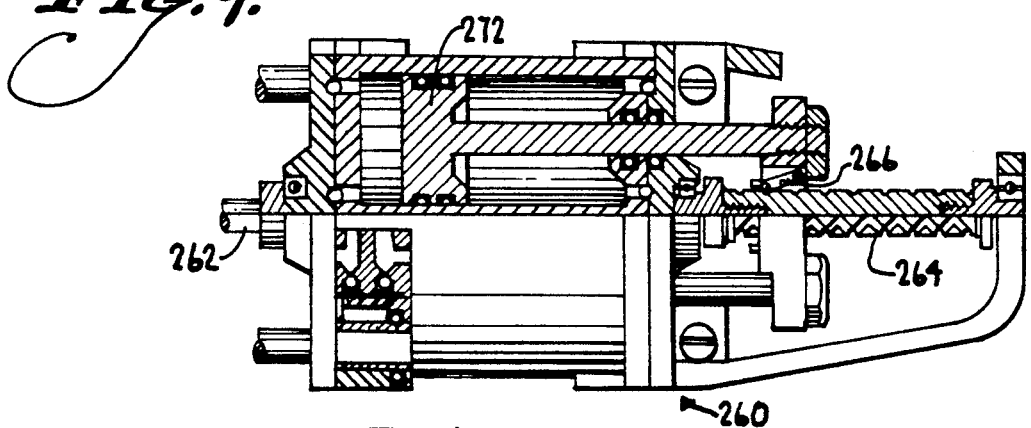
FIG. 11 is a partial section view of a miniature hydraulic pump for driving the actuators according to the invention.

The drive cylinders or actuation cylinders are preferably hydraulic. FIG. 11 is a partially cut away elevation view of a miniature hydraulic pump 260 which can provide sufficient pressure and flow to operate the exoskeleton device. Of course it is possible to scale the unit up as needed. The pump is coupled to a central shaft 262, which can be rotated by a battery powered electric motor (not shown in FIG. 11). A double helix slot pattern having end sections connecting the opposite helices is formed along a driving section 264 of shaft 262, for guiding a follower bushing 266 in a reciprocating motion. The follower bushing has one or more pins which ride in the slot, being driven with rotation of shaft 262 in one direction to the end of the slot pattern then around the end connection to the opposite pitch helix, which drives the follower bushing in the other direction as the shaft continues to rotate in the same direction, and so on. One or more pistons 272 are coupled by shafts to the follower bushing, the pistons 272 being reciprocated in their cylinders to develop hydraulic pressure and from an inlet to an outlet by means of check valves as known in the art.

Figure 13:
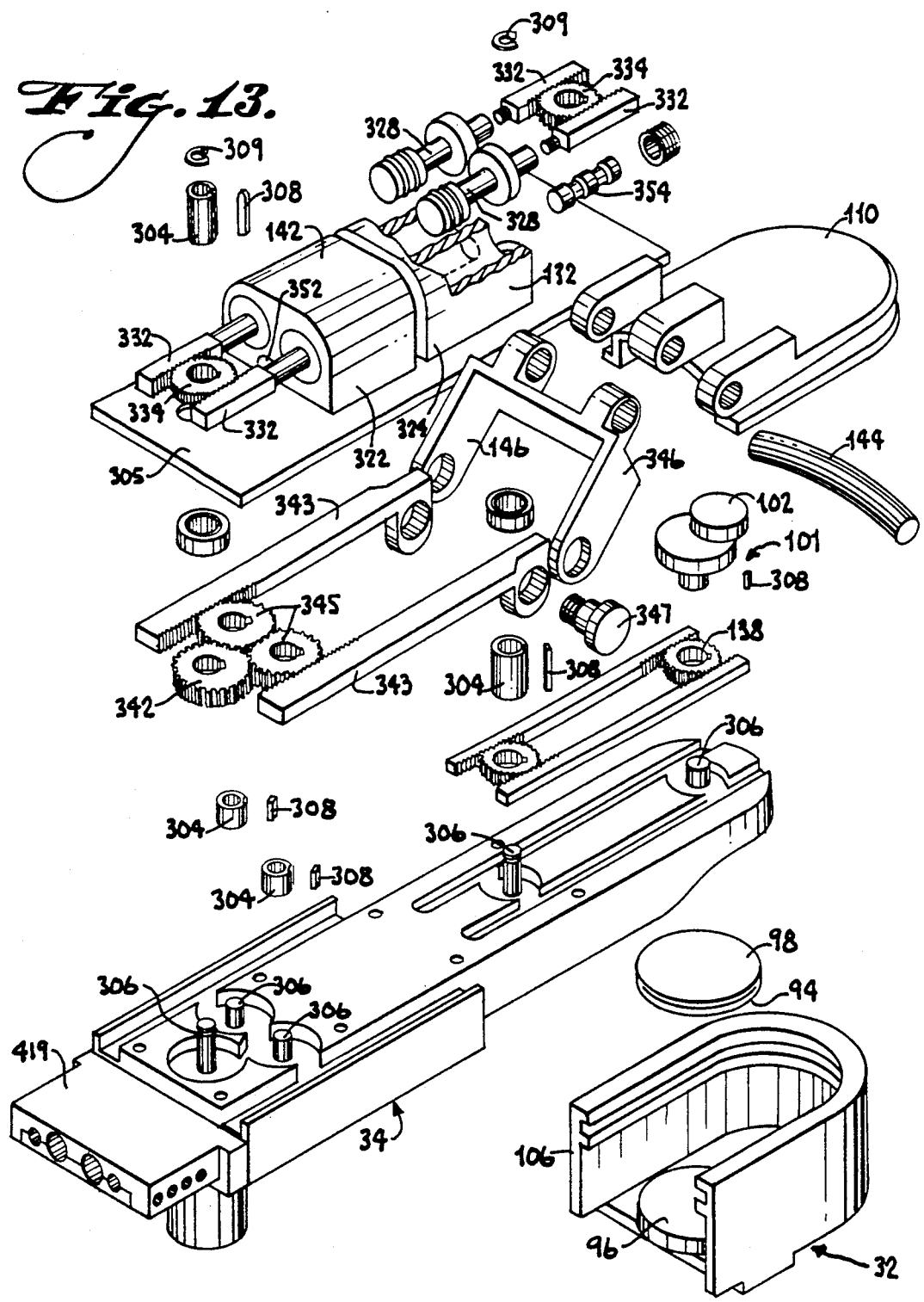
FIG. 13 is an exploded perspective view showing the operative elements of a preferred joint mechanism according to the invention, adapted for three degrees of freedom around a displaced center of rotation.

FIG. 13 illustrates a particularly compact embodiment of a three degree joint according to the invention, for general application to the three degree joints 62 which are employed at various parts of the exoskeleton. The adduction and medial drive assemblies are illustrated in detail. The flexion drive assembly is not shown in detail in FIG. 13; however, as in FIGS. 1 and 12 or 3-7 the flexion drive assembly involves a gear or sprocket arrangement arranged to rotate the joint housing 106 around a flexion axis which intersects the center point of the biological joint. In FIG. 13, only the joint housing portion of upper frame member 32 is shown.

The lower frame member 34 is provided with a base panel 302 having a number of depressions for receiving gears and sliding members associated with the adduction and medial drivers. The hydraulic cylinders for actuating the drivers are mounted on a cover panel 304, with the pinions of rack and pinion arrangements being rotationally coupled to corresponding rack and pinion arrangements disposed in the depressions of the base panel 302. This rotational coupling is provided by slotted bushings 304 which rotate on posts 306, and are coupled to the respective rack and pinion arrangements of the base panel 302 and the cover panel 304 by keys 308. C-clips 309 are provided for holding the respective pinions and bushings on their posts 306.

The hydraulic cylinders, which as noted above are preferably provided in pairs, comprise dual cylinder housings 322, 324, which can be bolted to or integral with the cover panel 304 and receive oppositely-acting piston assemblies 328. The piston assemblies include reciprocable shafts which can be attached threadably to the racks 332 which move the cover panel pinions 334. The dual cylinder housings 322, 324 can also define the cylinder part of control valves 352, wherein a valve body 354 is movable for proportionately controlling the application of pressure from the hydraulic pressure source to the respective pistons.

For adduction drive, the rotation of the cover panel pinion also rotates base pinion 342, due to the common keyed connection to the bushing on the corresponding post 306. Whereas the two adduction slide bars 343 move in the same direction, the base pinion 342 is coupled to one of two intermediate gears 345, 345, for forcing slide bars 343 toward or away from the housing cover plate 110. The slide bars 343 are coupled to the adduction tie rod structure 346 by two shoulder bolts 347 (one being shown). Adduction tie rod 346 is hingeably coupled to cover plate 110 by adduction link pin 144, which is arched. Link pin 144 and the bores therefor in the housing cover 110 define an arc concentric with the biological joint, which allows the adduction drive to operate at any medial position within a limited range of medial displacement. The holes in the adduction tie rod structure 346 are oversized, allowing free pivoting around link pin 144.

The medial drive also has a rack and pinion arrangement on the cover panel 304 and the base panel 302, coupled by a slotted bushing and pin. The medial slide bars move in opposite directions for rotating the eccentric roller 102 relative to the post 306 to which the base of the roller structure is mounted. The eccentric roller structure is rotationally fixed relative to its base panel gear via a slotted bushing and pin. As the eccentric roller is moved, being carried in the longitudinal slot on the underside of joint housing cover 110 in FIG. 13, the housing cap as well as the joint housing 106 generally, are displaced along link pin 144 relative to the base panel. As the adduction drive extends or retracts the distance between link pin 144 and the adduction drive gears, the joint housing 106, and the upper frame member 32, are displaced relative to the biological joint center by sliding over the rounded surface of spacer 98, interposed between the joint housing 106 and the housing cap 110.

Figure 14:
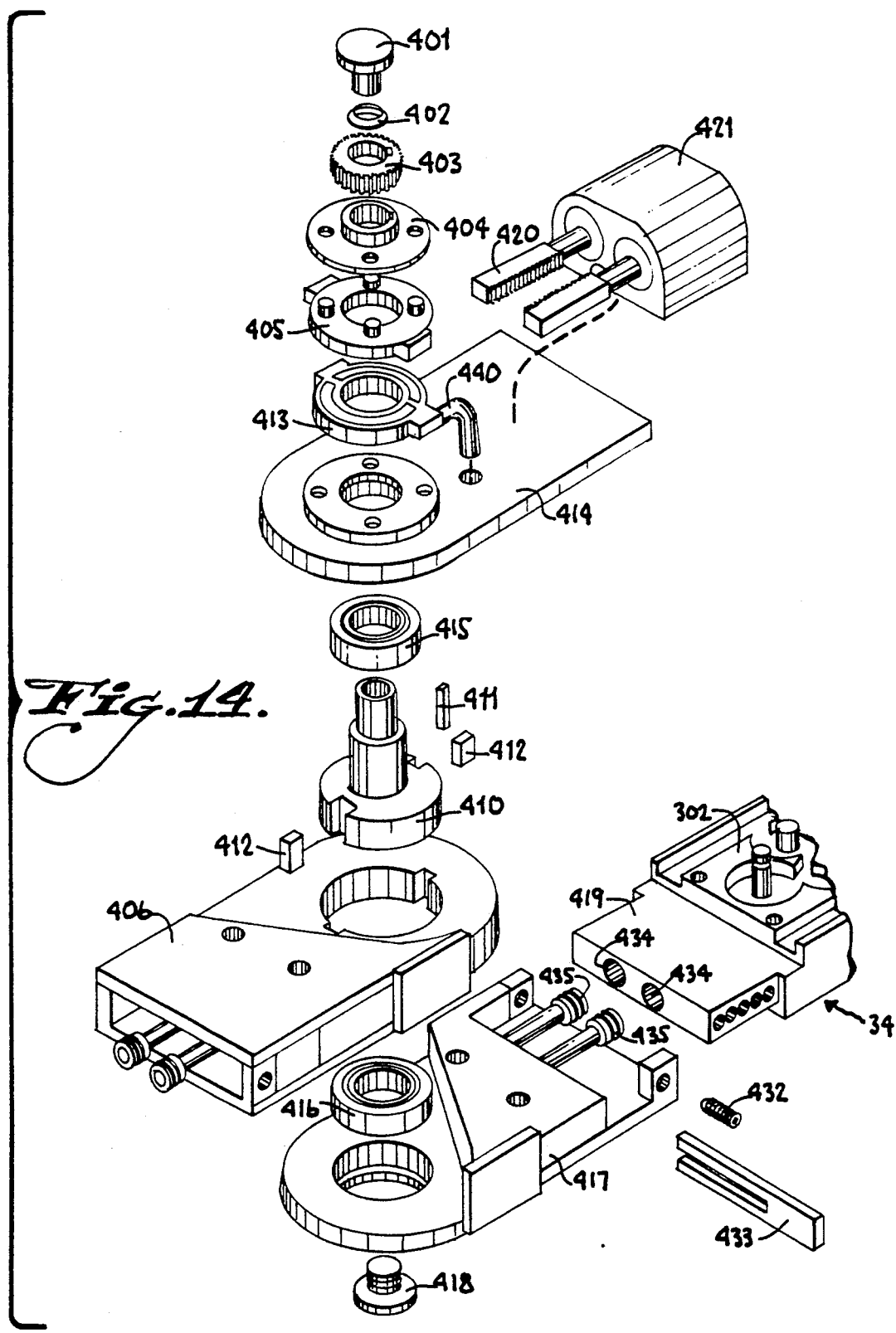
FIG. 14 is an exploded perspective view showing the operative elements of a preferred joint mechanism having one degree of freedom, for example for a knee or elbow, and including a sealed hydraulic passage traversing the joint mechanism.

In a relatively light duty application the connections between the hydraulic pump and the proportional valves leading to the respective cylinders can be made using flexible tubes external to the frame members. Preferably, for a more heavy duty and durable arrangement the hydraulic connections are made insofar as possible through passages formed by bores running longitudinally in the frame members 32, 34. Where necessary to bridge joints the hydraulic connections can be made using relatively short tubes flexible tubes traversing the joint and coupling the hydraulic line to the next successive frame member. In joints with only one degree of freedom such as the knee or elbow, it is possible to make the necessary hydraulic connections through a sealed passageway configuration through the joint, as shown in FIG. 14.

As noted above, the dual cylinder housing 421 can be bolted to or integral with the upper knee outer buttress plate 414, and the drive racks position a pinion or spur gear 403, which is keyed to the opposed knee member 406 by pin 411. More particularly, gear 403 is keyed to a knee shaft assembly 410 via pin 411 and the knee shaft assembly 410 is keyed to the opposed knee member 406 by pins 412, 412. One or both of the upper and lower leg members 302 (which can be the exoskeletal femur or tibia/fibula) can be adjustable in length for fitting a particular wearer. In the embodiment shown, leg member 302 has an extension plate 419 which can be received in a knee buttress plate 417 over a range of positions at which the two can be rigidly fixed via locking screws 432 (one being shown), preferably with a spacer 433 of appropriate width interposed for support. Hydraulic connections via bores 434 in leg member 302 are made with extension tubes 435, protruding from the buttress plate and having 0-ring seals for engaging bores 434. Opposed knee member 406 also includes similar extension tubes as shown.

A rotary hydraulic seal allowing bidirectional flow of hydraulic fluid through the joint is provided by alignable passages through the respective rotary element stacked on the knee shaft assembly 410 and compressed by securing bolt 401, Bellville spring 402, and opposed securing bolt 418, which compress the joint along its rotation axis. The extent of displacement permitted is limited by the abutting structures of buttress plate 417 and opposed member 406, namely between collinear and a maximum displacement.

A locking plate 404 prevents rotation of one side of a rotary hydraulic seal assembly having outer (upper) and inner (lower) parts. On the outer side, a lapped lower surface of outer seal element 405 mates with the lapped upper surface of an inner seal element 413. The bisected circumferential grooving of the inner seal element allows constant hydraulic fluid access to the ports in the outer rotary seal element 405, providing connection around a span of rotation of the knee. Pins on the underside of inner seal element 413 mate with holes in the upper knee outer buttress plate 414 to prevent rotation of the inner rotary hydraulic seal independently of the upper knee assembly. Items 415 and 416 are roller bearing assemblies, thrust-faced and press fitted into the knee buttress plates 414, 417 such that the thrust faces contact the large diameter faces on the lower knee shaft assembly 410. This arrangement provides for driven displacement of the knee and also provides two hydraulic connection lines 440 (one of which is shown) for supply and return, respectively, whereby hydraulic power can be made available at further distal joints such as the ankle joint, the hydraulic connections traversing the knee without requiring flexible lines which are subject to damage.

Energization of the respective actuator cylinders can be accomplished by sensing pressure applied by the wearer to inner surfaces of the limb cradles 38 using sensors 39, shown in FIG. 12, and applying power in the same direction using the respective actuator cylinders. One possibility is to electrically sense pressure applied in the three directions of freedom, and to electrically operate proportional valves for coupling hydraulic fluid to the cylinders. In the embodiment according to FIG. 15, pressure exerted by the wearer against spring biased contact C1 of sensor 39 is converted into corresponding levels of voltage, positive for increasing pressure and negative for decreasing pressure, by circuitry 192, which is a schematic representation of a pressure-to-voltage transducing mechanism. The sensed pressure information can be processed using servo control techniques to generate control signals applied via coils X1 and X2 to position a ferromagnetic body R1 of a center biased controller mechanism 212 for controlling proportional fluidic switch 214 having a fluidic plate F1. The controller mechanism 212 depicted comprises a cylindrical body with a fluid inlet central to its length, and fluid outlets at its ends, each leading to a control arm of fluidics switch 214. The bar R1 is close-fitting within the cylinder and is spring positioned such that the fluid inlet channel bisects the length of the bar, causing an equal restriction of fluid flow between the inner surface of the cylinder and the outer surface of the bar to the control arms of fluidic switch 214. Operationally, the direction and magnitude of displacement of bar R1 by coil assembly 193 causes unequal fluid flow rates to the control arms, which in turn causes proportionately unequal fluid flow rates between the output legs of fluidic switch 214. The output from fluidic switch 214 in turn positions the spool valve 242 of valve V1 by the fluid flow differential from fluidic switch 214 acting in conjunction with orifice plates 218 (01 and 02), which restrict return fluid flow, to cause a pressure difference on the two ends of spool valve 242. The spool valve 242 is thus moved the proper distance in the proper direction for coupling hydraulic fluid ar various flow rates to one paired set of actuators 66 which can then drive a gear arrangement 68 as shown in FIG. 16. It is possible with the control system shown to displace the actuators 66 in either direction at speeds proportional to the pressure applied to sensor 39, or to lock them at a present position by cutting off hydraulic fluid flow.

At system turn-on, fluidic plate 214 must deliver equal flow through each of its legs to spool valve 242 to prevent a sporadic twitch of robotic activity. At that moment the pressure being applied to the sensor element 39 is unknown and/or not subject to any positional variation by the wearer (who is not then obtaining any visual or sensory feedback regarding the pressure applied to the sensor). Accordingly, initialization under control of the microprocessor 194, acting by setting the position of control valve 212 using coils 193, sets a null point for fluid amplifier 214. Valve 212 is held at this position initially. At a predetermined time sufficient to allow the pressures in the system to reach operational levels, variations in position of sensor 39 (and preferably two opposed sensors) are converted into variations in the position of the output, allowing the apparatus to control joint position. Similar valving and sensing arrangements are provided for each opposed pair of actuation cylinders.

Figure 15:
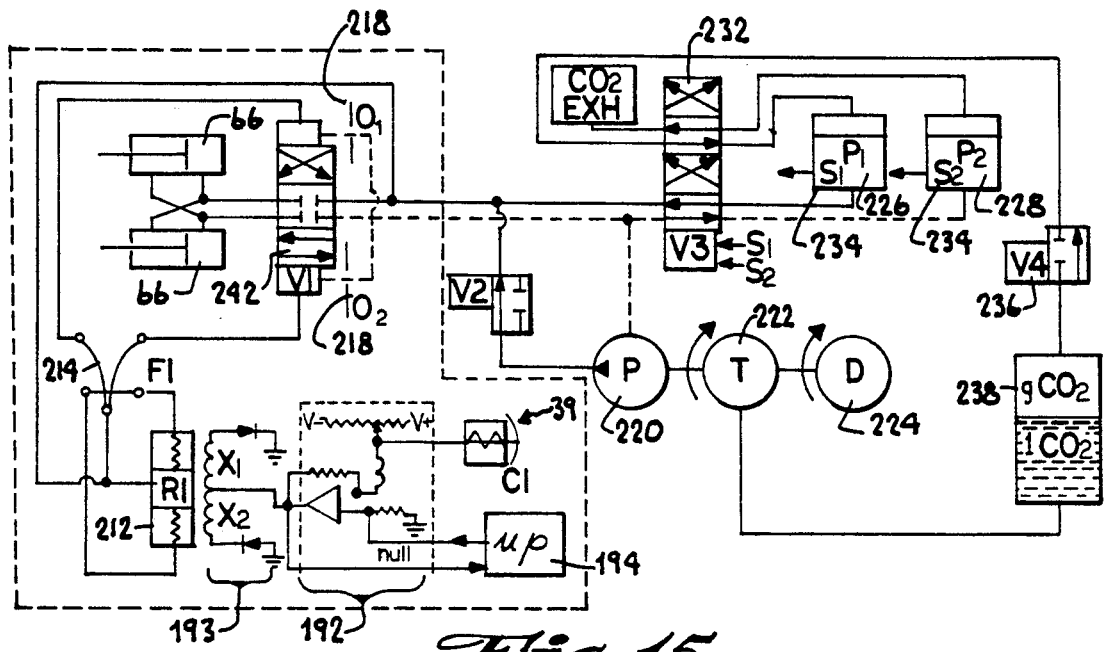
FIG. 15 is a schematic block diagram illustrating a control arrangement for the actuators.
Figure 16:
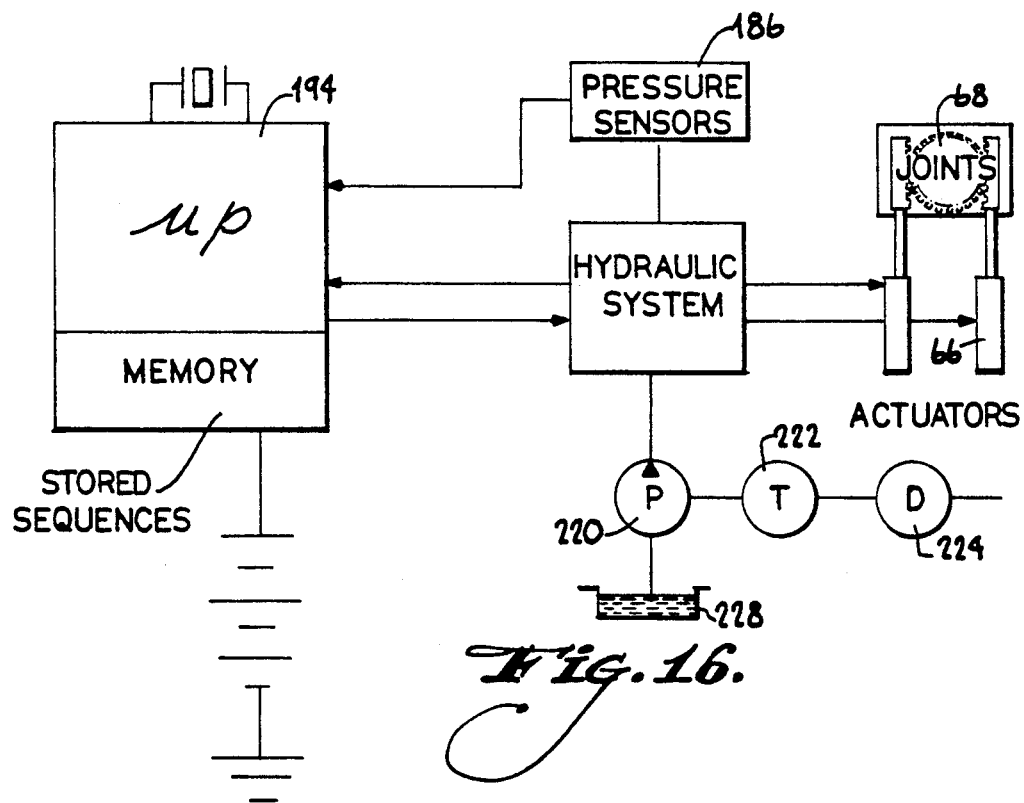
FIG. 16 is a schematic block diagram illustrating an embodiment of the invention comprising a programmed controller.

The control arrangement shown in FIG. 15 is an example of a control to be applied to one of the three degrees of freedom. A spool valve 242 is spring biased to a center position, where the actuators' 66 connections to the hydraulic lines are off. The spool valve 242 is moved to one side or the other by unequal fluid pressure on its ends, exerted by the wearer. The control valve 212 can be centered positively by a solenoid arrangement including two coils, or the position of the valve body can be set electrically using the two coils, using a proportional control signal developed, for example, via a digital to analog converter and amplifier, coupled to an output of a microprocessor 194.

Preferably the signal generated by circuitry 192 is converted into digital data by additional circuitry which is not shown, and coupled to an input of the microprocessor controller 194, shown in FIG. 16. The microprocessor provides outputs to control the position of hydraulic valve body V1 and optionally can be arranged to read back programmed sequences of operation from memory in addition to or instead of the control command information developed from monitoring the pressure of the wearer's limbs against spring biased contacts. The fluidic or microprocessor controlled valves couple a controllable amount of hydraulic power to the actuator cylinders through spool valve 242, which can be a center-off proportional valve.

For flexion/extension, at least one contact C1 is provided at either the front or rear of the wearer's limb, and preferably at both. For adduction/abduction the contact C1 is placed laterally. Two contacts on opposed sides of the wearer's limb can be used differentially, whereby the control arrangement is responsive to differences and is independent of pressure due to the potentially-variable tightness of the cradle and strap limb restraints. For the medial direction, rotational pressure exerted by the wearer can be sensed and transmitted using a similar arrangement wherein an operator for the control valve is coupled at a tangent to the center of rotation.

Referring to FIGS. 15 and 16, the primary power elements can include the hydraulic pump 220, a drive turbine 222, a dynamo 224, an accumulator 226, a reservoir 228, a reversing valve 232, two reversing switches 234, and isolation valves 236. The dynamo 224 provides some system electrical power; however, in the event of a turbine failure the dynamo 224 serves as a battery powered emergency drive motor for the pump 220. The accumulator 226 and reservoir 228 are topped with a piston and coupled to a source 238 of pressurized gas such as $CO_2$, which pressurizes the accumulator-reservoir system to cushion shocks and to store energy.

Figure 17:
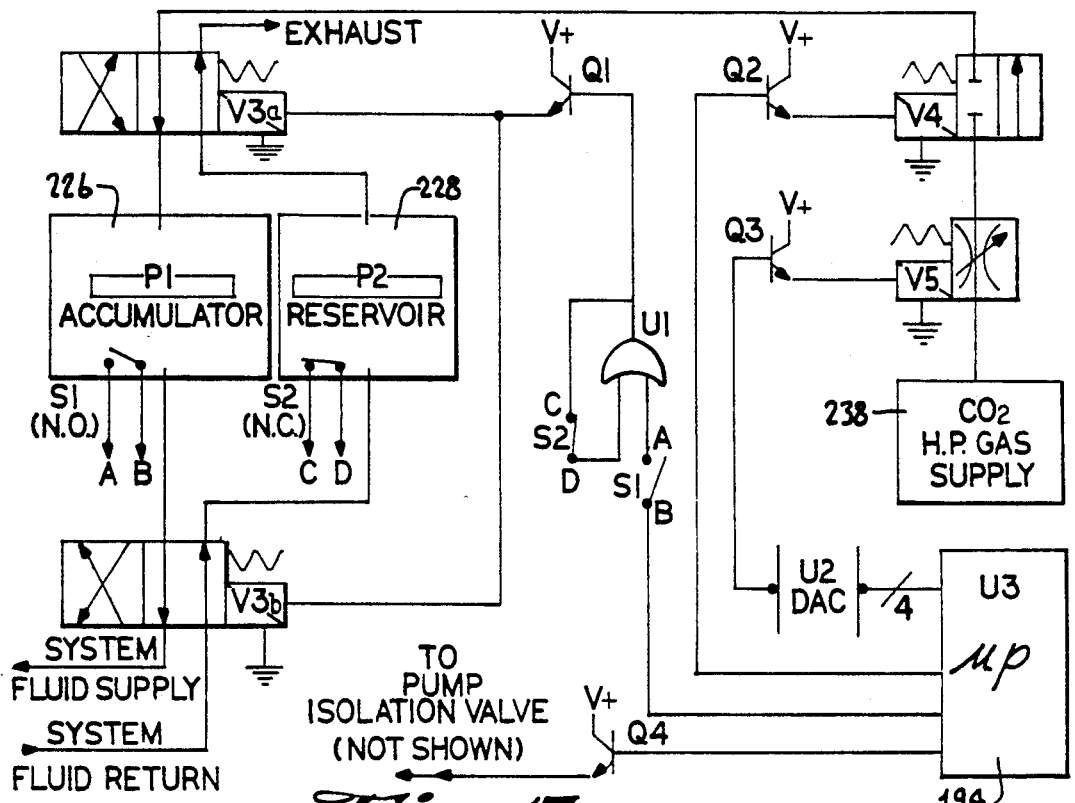
FIG. 17 is a schematic block diagram illustrating an embodiment including an emergency backup hydraulic supply and controller therefor; and, FIG. 18 is a schematic logical diagram illustrating a sensing and control arrangement according to the invention, adapted for simulating the effect of gravity while under power.

FIG. 17 functionally illustrates an arrangement for taking advantage of high pressure gas (e.g., $CO_2$) supply 238, also shown in FIG. 15. If the hydraulic pump 220 fails, the microprocessor controller 194 closes valve 236 (V2, see FIG. 15) to isolate the hydraulic pump 220 and opens valve V4 to allow high pressure gas to drive the piston in the accumulator 226 downward, at a pressure which can be controlled by microprocessor 194 via a control valve V5. The high pressure gas, in connection with the accumulator and reservoir can be arranged to continue system operation for a limited time following a hydraulic power supply failure. In the event of a failure the high pressure gas provides (through valve V3) a continued fluid supply to the system. Fluid returns from the system through valve V3 to the reservoir 228, causing its piston to rise. As the accumulator piston nears the bottom of its range, it closes the normally-open Hall effect switch S1, actuating valve V3, which switches the high pressure gas to the top of the reservoir; the fluid supply line to the bottom of the reservoir; releases the pressurized gas above the accumulator piston; and switches the fluid return line to the bottom of the accumulator. The outputs of microprocessor 194 drive transistors Q1-Q3 for operation of solenoids which actually position the respective valves V1-V5. High pressure gas now drives the piston in the reservoir downward, maintaining a continued fluid supply to the system. Fluid now returns from the system to the accumulator, causing its piston to rise and re-open switch S1. As the reservoir piston nears the bottom of the reservoir, it opens the normally closed Hall-effect switch S2, which clears the boot-strapped OR gate U1, causing valve V3 to deactivate and return by spring pressure, to its original position, beginning a new cycle. In this manner, the accumulator and the reservoir function as an emergency pump in order to maintain mobility of the exoskeleton, and enabling the wearer to move to a position of safety prior to effecting repairs. By controlling the application of pressure from the gas supply to the system via the microprocessor in the event of failure, it is possible to choose a brief period of continued mobility at the maximum power available from the gas supply, or a longer period at lower power, as well as intermediate values in the range, as may be appropriate in the wearer's particular circumstances.

Figure 18:
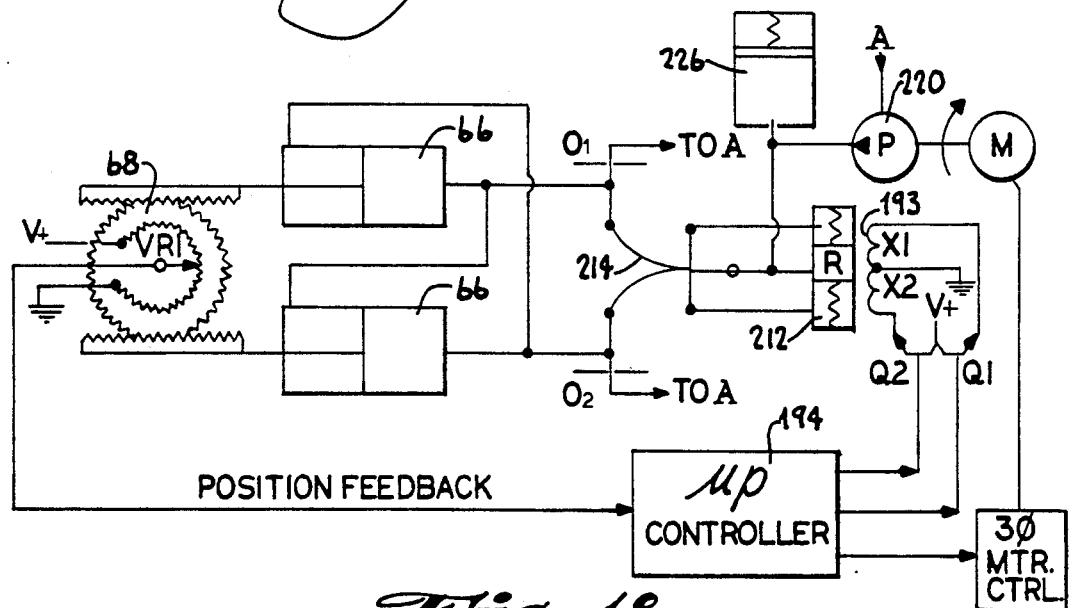

Operating the apparatus of the invention under control of sensors for limb pressure may require a period of training, particularly because the wearer is accustomed to moving about in the influence of gravity. The power assist apparatus of the invention can be scaled to a power required for a particular use, which may disproportionately relieve the wearer of the influence of gravity, making coordinated movements difficult without practice. With reference to FIG. 18, the microprocessor can be arranged to sense the present position of the limbs via joint angle sensors VR1, which may be potentiometers or the like affixed to the joint gear arrangements 68, and to provide a retarding influence in a downward direction to simulate the effect of gravity on the limbs of a person without a power assist apparatus. To perform such simulation, the microprocessor can be programmed with an algorithm for calculating the vector effect of gravity. FIG. 18 illustrates such an embodiment and FIG. 13 shows where a rotational angular sensor can be located (for sensing adduction displacement in this example). Similarly, potentiometers or the like associated with the drive gears can sense joint position. The microprocessor, keeping track of the displacement vector of each of the limbs, adjusts its control output to provide a simulation of gravity in an amount proportionately related to the extent of power assist. Similarly, the microprocessor preferably senses pressure in the accumulator 226 and varies the pump fluid delivery rate accordingly to maintain a constant system pressure.

Wearer motion information can be obtained by differentiating angular position information. For each degree of freedom, and each joint, an inertial component can be calculated, and the gravitational vector can be subtracted. During "downward" motion the gravitational adjustment complements the wearer's motion, and the wearer must adjust to maintain a desired joint motion in the same manner as the wearer normally responds to the influence of gravity. For an upward motion the gravitational adjustment reduces or resists the extent of wearer motion, likewise requiring adjustment. The gravitational adjustment to the powered motion defined by the wearer's motion can be applied continuously, or reduced to zero when motion is stopped.

In a simplest embodiment, the invention requires a hydraulic source and means for coupling a sensing valve to the actuation cylinders to control the direction and force of displacement of the frame members coupled to the wearer at a joint. Whereas mobility is one objective, battery power is preferred. It is also possible to obtain at least some mobility by coupling the system to a fixed hydraulic pump, allowing the wearer to move about within the range of connecting lines coupled to the pump.

In an embodiment wherein the powered exoskeleton of the invention is primarily intended to generally increase the power, speed or stamina of a healthy wearer, it is necessary to include a full range of powered joints, as shown in FIG. 1. Such an embodiment is appropriate, for example, to allow a soldier to move about in heavy body armor, or to manipulate the weight of a heavy weapon or a store of ammunition. The lower body embodiment of FIG. 2 is more suited to the needs of an invalid or the like, where the objective is simply the ability to move about. The invention is also applicable to power assist devices applied to individual joints.

By including the microprocessor controller and means for sensing joint position, it is also possible to operate the apparatus without the input from pressure sensors. For paraplegics, who may be unable to exert any pressure on a sensing apparatus, the microprocessor can be programmed to effect stored sequences of movements. In particular, for moving between sitting and standing positions, for walking, and for climbing stairs, the microprocessor can be programmed to effect the necessary motions. Preferably the microprocessor can also store a sequence of motions, and thus can be programmed to repeat a sequence entered under control via the pressure sensors, when sensor input is not available.

As shown in FIG. 1, the pump, accumulator and reservoir as well as the control apparatus can be arranged on the rear of the pelvis. The emergency gas supply, shown in dotted lines, can be carried on the back. A battery pack can be arranged in a torso-encircling belt. As also shown in FIG. 1, additional means for grasping under power are possible for the hands. Alternatively, various tools, weapons, grasping or other implements can be mounted on the arms or elsewhere as appropriate, for control using the manual action simply of the wearer's bare hands.

The invention having been disclosed, a number of variations on the concept will occur to persons skilled in the art. The invention is intended to encompass the preferred embodiments, as well as a range of equivalents and routine variations. Reference should be made to the appended claims rather than the discussion of preferred exemplary embodiments, in order to assess the scope of exclusive rights in the invention claimed.

I claim:

1. An exoskeletal robotic device adapted to supplement relative movement between at least two substantially rigid biological skeletal members coupled at a biological joint of a wearer, the biological joint being rotatable around three mutually perpendicular axes intersecting at a center of the biological joint, the mechanical joint comprising:

first and second frame members including means for attachment to outer surfaces of the skeletal members;

a mechanical joint means for coupling the first and second frame members, the mechanical joint means defining a center of relative rotation of the first and second frame members about three mutually perpendicular axes, the center of relative rotation of the frame members being displaced from the outer surfaces of the skeletal members to correspond in position with the center of the biological joint;

the mechanical joint means including a plurality of spherical guide surfaces operably connected to a defining slidable connections between the frame members, the spherical guide surfaces each having a radius intersecting the center of the biological joint; and, an extension shaft and journal coupling the frame members, the extension shaft defining a longitudinal axis intersecting the center of the biological joint and guiding motion of the biological joint in flexion and extension.

2. The exoskeletal robotic device according to claim 1, further comprising at least one actuation device coupled between the first and second frame members and operably connected to said mechanical joint means, and means for providing power to the actuation device for rotating the first and second frame members about said center of the biological joint.

3. The exoskeletal robotic device according to claim 2, further comprising at least one pressure sensor disposed on said frame member, the pressure sensor including means for enabling operation of at least one actuation device as a function of pressure on the pressure sensor.

4. The exoskeletal robotic device according to claim 2, further comprising a microprocessor controller connected to and operable to control at least one actuation device.

5. The exoskeletal robotic device according to claim 3, wherein at least one pressure sensor disposed on said frame members is coupled to a microprocessor controller such that the controller is operable to enable operation of at least one actuation device as a function of pressure on the pressure sensor.

6. The exoskeletal robotic device according to claim 1, wherein one of the spherical surfaces guides the joint in abduction and adduction and another of the spherical surfaces guides the joint in lateral and medical displacement.

7. The exoskeletal robotic device according to claim 1, further comprising at least three actuation devices coupled between the first and second frame members for driving the mechanical joint in three mutually perpendicular directions, each of the actuation devices being coupled to means for providing power to the actuation device for rotating the first and second frame members about the center of the biological joint.

8. The exoskeletal robotic device according to claim 7, comprising independently controllable opposed actuation devices for each of the three mutually perpendicular directions.

9. The exoskeletal robotic device according to claim 8, further comprising a microprocessor controller connected to and operable to control the actuation devices.

10. The exoskeletal robotic device according to claim 7, further comprising a plurality of pressure sensors disposed on said frame members, the pressure sensors including means for enabling operation of the actuation deices as a function of pressure on the pressure sensors.

11. The exoskeletal robotic device according to claim 10, wherein the plurality of pressure sensors disposed on said frame members are coupled to a microprocessor controller such that the controller is operable to enable operation of the actuation devices as a function of pressure on the pressure sensors such that the device applies power to the biological joint to supplement power applied by the wearer.

12. The exoskeletal robotic device according to claim 11, wherein the actuation devices comprise hydraulic cylinders, and further comprising a hydraulic pump coupled to the cylinders via valves operable in response to signals generated by the controller.

13. The exoskeletal robotic device according to claim 12, wherein the controller includes means for executing at least one predetermined sequence of operations independently of signals from the sensors.

14. The exoskeletal robotic device according to claim 13, wherein the predetermined sequence of operations is chosen from a natural sequence of human motions and reflects a full natural range thereof.

15. The exoskeletal robotic device according to claim 13, wherein said predetermined sequence of operations is chosen from the group consisting of standing from a sitting position, sitting from a standing position, ambulating, and traversing stairs.

16. The exoskeletal robotic device according to claim 12, wherein the controller includes means for recording at least one sequence of operations effected under control of the sensors, and means for executing said sequence of operations thereafter independently of signals from the sensors.

17. The exoskeletal robotic device according to claim 1, further comprising a plurality of additional frame members and mechanical joints, coupled together to form at least part of a supplemental skeleton for wear by a human.

18. The exoskeletal robotic device according to claim 17, wherein the plurality of frame members and mechanical joints define at least a pelvic and leg portion of the supplemental skeleton.

19. The exoskeletal robotic device according to claim 17, wherein the plurality of frame members and mechanical joints define at least a torso and arm portion of the supplemental skeleton.

20. The exoskeletal robotic device according to claim 1, further comprising a plurality of additional frame members and mechanical joints, coupled together to form at least part of a supplemental skeleton for wear by a human, defining at least part of a pelvic and leg portion and at least part of a torso and arm portion of the supplemental skeleton, independently controllable opposed actuation devices for each of three mutually perpendicular direction of movement being connected to each of said mechanical joints of the supplemental skeleton, and pressure sensitive output means on the frame members for sensing pressure applied by the wearer being coupled to the actuation devices for controlling powered movement.

21. The exoskeletal robotic device according to claim 20, wherein the pressure sensitive output means on the frame members are coupled to a microprocessor controller such that the controller is operable to exert pressure in a direction of sensed pressure for assisting in movements directed by the wearer.

22. The exoskeletal robotic device according to claim 1, further comprising a plurality of additional frame members and mechanical joints, coupled together to form at least part of a supplemental skeleton for wear by a human, defining at least part of a pelvic and leg portion and at least part of a torso and arm portion of the supplemental skeleton, independently controllable opposed actuation devices for each of three mutually perpendicular directions of movement connected to each of said mechanical joints of the supplemental skeleton, and a microprocessor controller being coupled to the actuation devices for controlling powered movement.

23. A mechanical joint device coupling first and second frame members and allowing rotation of the second frame member relative to the first frame member on three rotation axes, the three rotation axes intersecting at a common point, the second frame member being rotatable about any one of the rotation axes independently and about two or more of the rotation axes concurrently via couplings located remote from the point of intersection of the three rotation axes, the joint device comprising:

a first coupling forming an inner concave-faced disk defining a portion of a hemisphere concentric with the point of intersection, the first coupling being attached to the second frame member, and an outer convex-faces disk defining a portion of a hemisphere concentric with the point of intersection, the outer convex-faces disk of the first coupling being rotatably coupled to the second frame member;

a second coupling forming an inner convex-faces disk defining a portion of a hemisphere concentric with the point of intersection, the inner convex-faces disk of the second coupling being fixed to the first frame member via a shaft defining an axis intersecting the point of intersection of the three rotation axes, said inner convex-shaped disk of the second coupling being shaped to complement the inner concave-faced disk of the first coupling, the second coupling further comprising an outer plate having an inner surface defining a concavity and an arching slot recessed in the inner surface defining a portion of a hemisphere concentric with the point of intersection, said arching slot being dimensioned for sliding engagement with the outer convex-faced disk of the first coupling, and structural means rotatably attached to said shaft for connecting the outer plate of the second coupling to the first frame member;

at least one adduction/abduction mechanism including means coupled to the first coupling for causing adduction and abduction of the second frame member, relative to the first frame member, around the point of intersection;

at least one lateral/medial mechanism attached to the second frame member and to the outer convex-faces disk of the first coupling for causing lateral and medial displacement of the second frame member relative to the first frame member around the point of intersection, due to a lateral constraining action of the outer convex-faced disk of the first coupling and the arching slot of the second coupling;

at least one flexion/extension mechanism movably attached to the first frame member and engaged with the structural means rotatably attached to said shaft fixing the inner convex-faced disk of the second coupling to the first frame member, the at least one flexion/extension mechanism causing flexion and extension of the second frame member relative to the first frame member, around the point of intersection;

means for attaching the first and second frame members to biological members coupled at a biological joint, such that the point of intersection of the three rotation axes coincides with an operational center of the biological joint, whereby the first and second frame members are constrained to move in correspondence with the biological joint.

24. The mechanical joint according to claim 23, further comprising powered means for coupling to and operatively driving the adduction/abduction mechanism, the lateral/medical mechanism and the flexion/extension mechanism, respectively.

* * * * *

UNITED STATES PATENT AND TRADEMARK OFFICE
CERTIFICATE OF CORRECTION

PATENT NO. : 5,282,460
DATED : February 1, 1994
INVENTOR(S) : Kenneth Boldt

It is certified that error appears in the above-indentified patent and that said Letters Patent is hereby corrected as shown below:

Column 1, line 36, insert a period --.-- after "members"

Column 3, lines 21 and 22, delete "As a result, any from the center of the biological hip joint."

Column 16, line 10, delete "." after --accumulator--.

Column 18, line 18, change "a" to read --and--.

Column 18, line 55, change "medical" to read --medial--.

Column 19, line 8, change "deices" to read --devices--.

Column 20, line 33, change "faces" to read --faced--.

Column 20, line 35, change "faces" to read --faced--.

Column 20, line 38, change "faces" to read --faced--.

UNITED STATES PATENT AND TRADEMARK OFFICE
CERTIFICATE OF CORRECTION

PATENT NO. : 5,282,460
DATED : February 1, 1994
INVENTOR(S) : Kenneth Boldt

It is certified that error appears in the above-indentified patent and that said Letters Patent is hereby corrected as shown below:

Column 20, line 40, change "faces" to read --faced--.

Column 20, line 64, change "faces" to read --faced--.

Column 22, line 11, change "medical" to read --medial--.

Signed and Sealed this

Nineteenth Day of July, 1994

Attest:

BRUCE LEHMAN

Attesting Officer     Commissioner of Patents and Trademarks